(12) United States Patent
Fink

(10) Patent No.: US 7,481,534 B2
(45) Date of Patent: Jan. 27, 2009

(54) OPTOMECHANICAL AND DIGITAL OCULAR SENSOR READER SYSTEMS

(75) Inventor: Wolfgang Fink, Montrose, CA (US)

(73) Assignee: California Institute of Technology, Pasadena, CA (US)

( * ) Notice: Subject to any disclaimer, the term of this patent is extended or adjusted under 35 U.S.C. 154(b) by 127 days.

(21) Appl. No.: 11/488,427

(22) Filed: Jul. 17, 2006

(65) Prior Publication Data
US 2007/0019156 A1 Jan. 25, 2007

Related U.S. Application Data

(60) Provisional application No. 60/700,001, filed on Jul. 15, 2005, provisional application No. 60/781,237, filed on Mar. 10, 2006.

(51) Int. Cl.
*A61B 3/00* (2006.01)
*A61B 3/02* (2006.01)
(52) U.S. Cl. ........................ 351/200; 351/222
(58) Field of Classification Search ................ 351/200, 351/205, 210, 222–223
See application file for complete search history.

(56) References Cited

U.S. PATENT DOCUMENTS 6,579,235 B1 6/2003 Abita et al.
6,921,169 B2 7/2005 Su et al.
2003/0117580 A1 6/2003 Franz et al.
2005/0268722 A1* 12/2005 Tai et al. ..................... 73/715
2006/0183986 A1* 8/2006 Rice et al. ................... 600/319

FOREIGN PATENT DOCUMENTS

WO WO-2004/036268 4/2004

OTHER PUBLICATIONS

Kinch, Richard J., "Making Digital Camera Microscope Adapters" [retrieved on Jun. 5, 2006] Retrieved from the Internet: URL:http://www.truetex.com/micad.html.
Pan, Jason, "ITRC develops 'X-Loupe' micro-photo digital camera", Feb. 23, 2006, [retrieved on Jun. 5, 2006] Retrieved from the Internet: URL:http://www.itrc.org.tw/Bulletin/Media/showmedia.php?idno=1140688804.
Cokin Magnefix Information, [retrieved on Jun. 5, 2006] Retrieved from the Internet: URL:http://www.cokin.com/ico12-index.html.

* cited by examiner

*Primary Examiner*—Ricky L Mack
*Assistant Examiner*—Dawayne A Pinkney
(74) *Attorney, Agent, or Firm*—Ropes & Gray LLP

(57) ABSTRACT

System, methods, and devices are described for eye self-exam. In particular, optomechanical and digital ocular sensor reader systems are provided. The optomechanical system provides a device for viewing an ocular sensor implanted in one eye with the other eye. The digital ocular sensor system is a digital camera system for capturing an image of an eye, including an image of a sensor implanted in the eye.

25 Claims, 11 Drawing Sheets

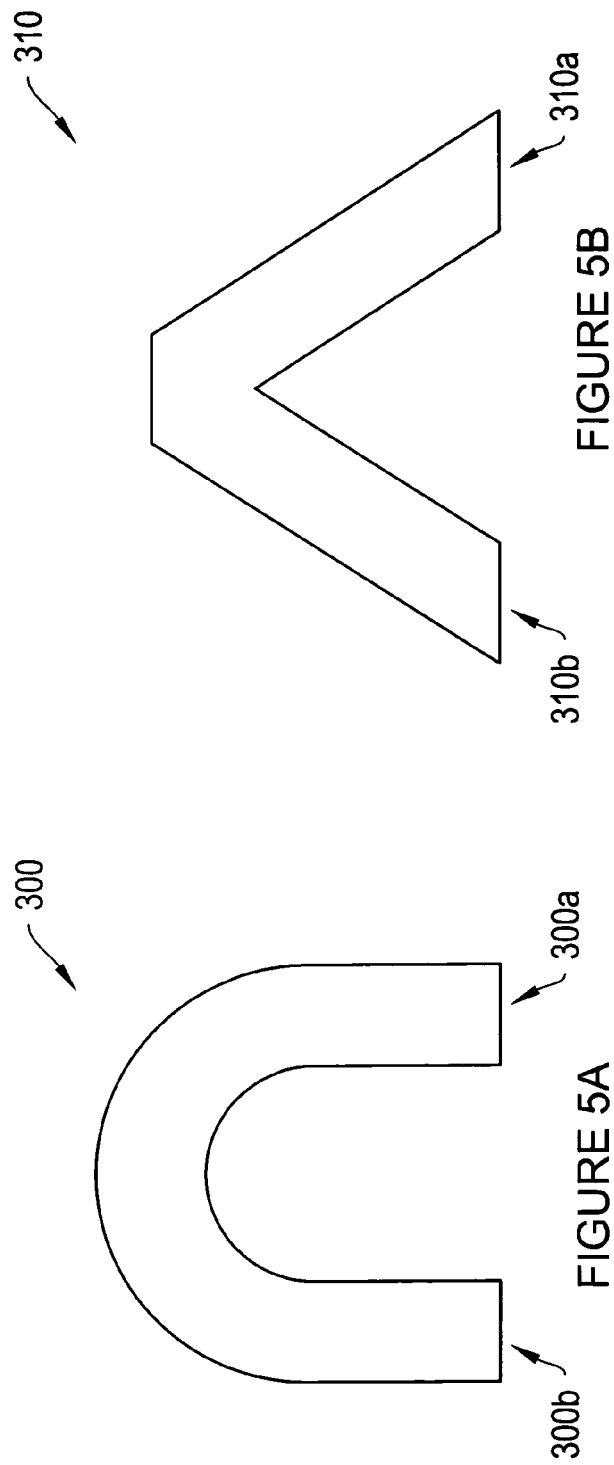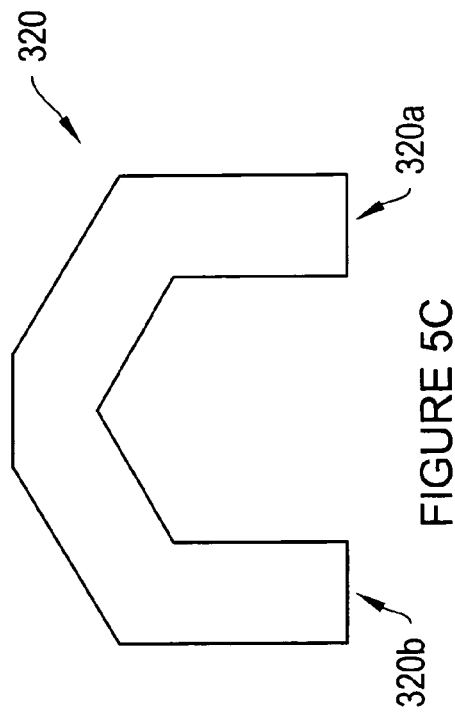
FIGURE 5A
FIGURE 5B
FIGURE 5C

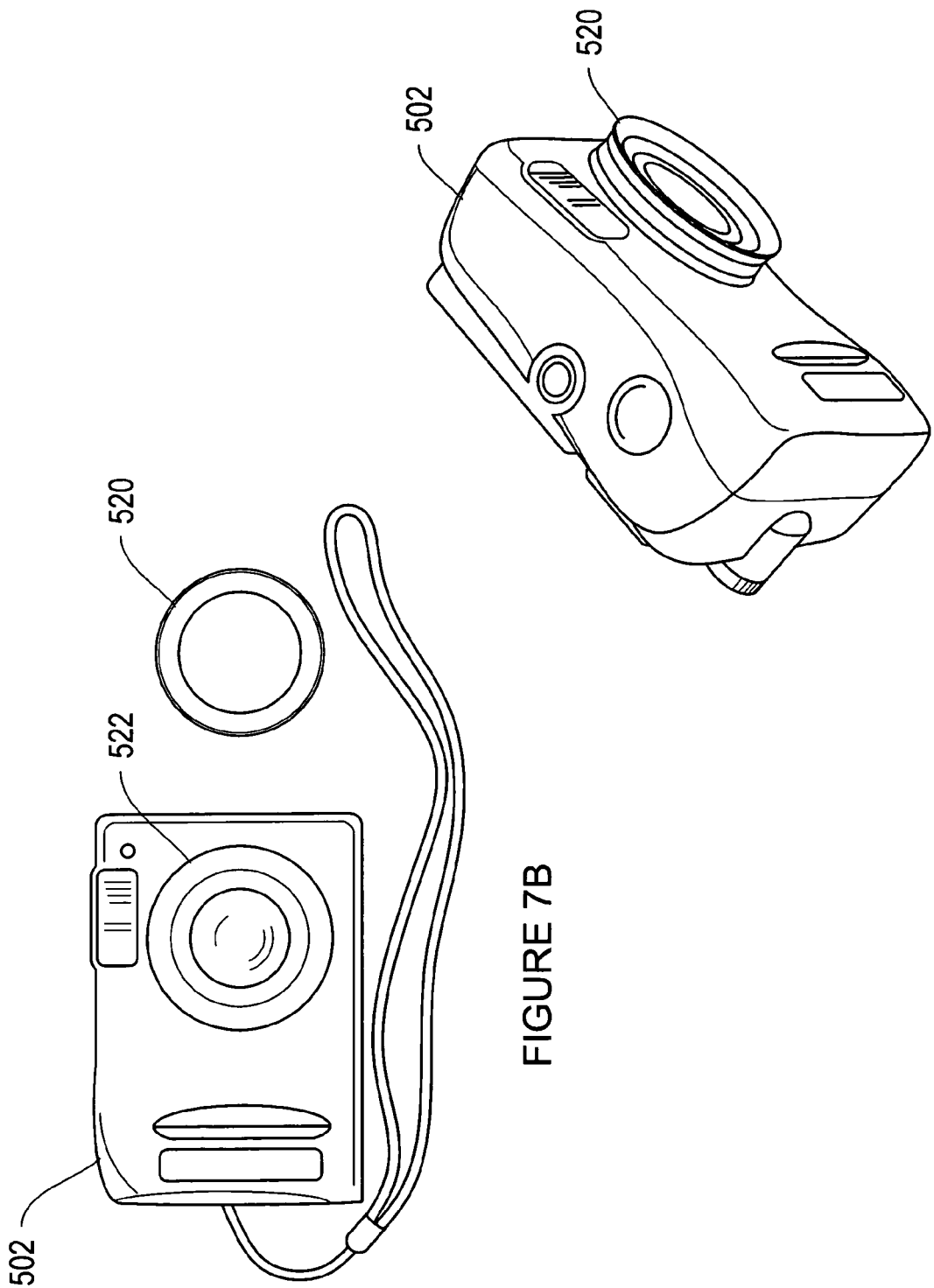

OPTOMECHANICAL AND DIGITAL OCULAR SENSOR READER SYSTEMS

CROSS REFERENCE TO RELATED APPLICATIONS

This application claims priority to U.S. Provisional Patent Application No. 60/700,001, entitled "External Reader System for Devices Implanted in the Eye" filed on Jul. 15, 2005 and to U.S. Provisional Patent Application No. 60/781,237, entitled "Microscope-like Capability for Consumer Digital Cameras" filed on Mar. 10, 2006, the entirety of which are hereby incorporated by reference.

BACKGROUND OF THE INVENTION

Glaucoma is a disease affecting millions of people in the US alone every year. Elevated intraocular pressure (IOP), the most common cause of glaucoma, slowly kills the ganglion cell axons (which collectively form the optic nerve) affecting the peripheral visual field and progressing to the center. If untreated, glaucoma leads to blindness. In general, visual field loss caused by glaucoma is irreversible.

There are a number of external eye pressure measuring devices. Typically, these devices indent the cornea either directly, by contacting it, or indirectly, by a non-contact method (i.e., pneumatic displacement "air puff"), to measure IOP. For example, a Tono-pen manufactured by Medtronic Solan (Jacksonville, Fla.) utilizes micro strain gage technology with battery power and a 1.5 mm transducer tip to gently contact the cornea and display the average of four independent readings along with a statistical coefficient. Both contact and non-contact tonometers are very dependent on the eye wall and corneal rigidity and can be inaccurate because these factors are not taken into account. In addition to the problems of imprecision with many of the external IOP measuring devices, many of these devices, especially those that contact the cornea, can only be administered in physicians' offices.

More reliable IOP measurements can be obtained from within the eye. A variety of devices have been proposed or developed for this purpose.

U.S. Pat. No. 6,579,235 issued on Jun. 17, 2003, the entire contents of which are incorporated herein by reference, discloses a device for passively measuring intraocular pressure of a patient. The device includes an in vivo sensor and an instrument external to the patient for remotely energizing the sensor, thereby permitting the instrument to determine the intraocular pressure. The device directly and continuously measures the intraocular pressure of a patient. The in vivo sensor in the intraocular pressure monitor includes a capacitive pressure sensor and an inductive component. An instrument, external to the patient, measures the pressure, provides readout of the pressure values, and determines the intraocular pressure.

U.S. Pat. No. 6,443,893 issued on Sep. 3, 2002, the entire contents of which are incorporated herein by reference, discloses another device for measuring intraocular pressure. The device includes a remote measuring device adapted to be implanted in an eye. The remote measuring device has a pressure sensor, a converter for converting sensor signals into information for wireless transmission, and a transmitter. The device also includes a receiver adapted to be located outside the eye for receiving information transmitted by the transmitter, and an evaluation device. The evaluation device converts information received from the transmitter into data expressing the intraocular pressure, and records the data. The remote measuring device also includes a data logger in which measurement data continuously supplied by the pressure sensor is stored and from which the measurement data is called up at certain times in operation of the converter.

Patent application Ser. No. 10/686492 filed on Oct. 14, 2003, the entire contents of which are incorporated herein by reference, discloses an optically powered and optically data-transmitting wireless pressure sensor, suitable for implantation in an eye and for monitoring the IOP continuously or on demand. The device may be placed in the anterior chamber of an eye, on the iris of an eye, on an intraocular lens, or on a glaucoma tube.

Most current IOP implants require an external component to receive information regarding the pressure. An optical implant may include a visual indication of IOP, which could be read by an eye care professional by looking into the patient's eye through a magnifying lens system. However, this may require frequent check-ups, which is inconvenient for many patients. Furthermore, several days or weeks may lapse between a change in implant status, such as detection of a high IOP, and the patient's next check-up, and eye or optical nerve damage may occur during this time.

While a conventional digital camera may be used to take a picture of an eye, both the tele-zoom and macro-mode (for shooting images up close, usually from a distance of about 20 cm) functions are insufficient for imaging an intraocular sensor.

SUMMARY OF THE INVENTION

The invention, in various embodiments, provides ocular sensor readers for a user to view or image an implant in the user's eye. According to one aspect, this is achieved through the use of an ocular exam device. The ocular exam device may be used to perform self-exams, or it may be used to examine another user's eye. According to one embodiment, the ocular exam device may be used to monitor a device implanted in an animal's eye.

According to one aspect, the invention provides an ocular self-exam device including a housing, with one or more lenses and one or more optical components positioned within the housing. The housing has first and second ends, which are sized and shaped for simultaneously positioning over the respective first and second eyes of a user. The one or more optical components are configured to form an optical pathway for guiding light entering at the first end of the housing to the second end of the housing.

According to one implementation, the ocular self-exam device includes a light positioned at the first end of the housing and configured to illuminate a target structure. The light may be positioned around at least one of the interior perimeter of the housing and the exterior perimeter of the housing. In one example, the housing has a circular cross-section and the light is annular. According to various embodiments, the light may be a visible light, an infrared light, or an ultraviolet light.

According to other implementations, the one or more lenses provide magnification of a target structure. For example, the one or more lenses may provide about 50 times magnification. In another example, the one or more lenses may provide between about 40 and about 80 times magnification.

In another implementation, the ocular self-exam device includes a focus control for focusing the one or more lenses on a target structure. The focus control may be manually adjusted by the user, or it may automatically adjust the one or more lenses to focus on a target structure. In one implementation, the ocular self-exam device also includes an autofocus sensor.

In various implementations, the ocular self-exam device includes a power supply and/or a barometer. The power supply and barometer may be coupled to the housing. The device may also include one or two eye cups attached to the first and/or second ends of the housing. The eye protectors may be plastic, soft plastic, rubber, or foam. The one or more eye cups may be configured for placing over an eye, and may prevent environmental light from entering at the first end of the ocular self-exam device.

According to one implementation, the one or more optical components includes one or more reflective surfaces. The reflective surfaces may be mirrors. According to one example, the reflective surfaces are positioned within the housing such that light entering from a first end of the housing is reflected on the surfaces and exits out the second end of the housing.

According to another implementation, the one or more optical components include an optical fiber. The optical fiber may be configured similar to an endoscope optical fiber and may transmit light and/or an image of a target structure from the first end of the housing through the optical fiber toward the second end of the housing.

In another implementation, the ocular self-exam device includes a width adjuster coupled to the housing for adjusting the distance between the first and second ends of the housing. The width adjuster may be used to adjust the width such that the first end may be placed over one eye of a user while the second end is simultaneously placed over the other eye of the user.

In a further implementation, the first and second ends of the housing include first and second openings of the housing, and at least one of the first and second openings comprises a transparent covering. The transparent covering may be constructed from, for example, glass and plastic. In one example, the transparent covering is a lens.

According to one configuration, the housing of the ocular self-exam device includes two or more substantially straight sides positioned in a first plane. In one particular example, the housing includes first, second and third sides, with the first and third sides substantially parallel to each other, and the second side positioned between and substantially perpendicular to the first and third sides, thus forming three sides of a rectangle.

In other configurations, the housing may be curved, semi-circular, u-shaped, v-shaped, or polygonal, and include first and second ends for placing over the eyes of a user.

According to another aspect, the invention provides a method for performing an eye self-exam. The method includes providing an optical pathway having first and second ends, positioning the first end of the optical pathway over a first eye of a user, positioning the second end of the optical pathway over a second eye of the user, identifying a sensor implanted in the first eye, wherein the sensor includes a level indicator, and detecting a level of the sensor.

According to one implementation, the sensor is a pressure sensor and may measure intraocular pressure. Similarly, the level may be a pressure level and may indicate the intraocular pressure level.

In another implementation, the level indicator includes one or more lights, which may indicate the level of the sensor. According to various examples, the one or more lights may indicate the level of the sensor by the color of the light, whether the light is turned on or off, whether or not the light is flashing, or by displaying a total pressure level. In other implementations, the level indicator includes a dial or a gauge. The dial or gauge may point to a number indicating total intraocular pressure level. In one example, the dial or gauge may include a colored background indicating if the pressure level is acceptable, borderline, or high. In still further implementations, the level indicator includes a digital read-out indicating the total intraocular pressure level. The digital read-out may be a light-emitting diode.

According to one implementation, the optical pathway of the method of eye self-exam includes one or more reflective surfaces. In another implementation, the optical pathway includes an optical fiber.

According to another aspect, the invention provides a device including a digital camera, a magnifying lens system coupled to the digital camera, and an eye cup coupled to the magnifying lens system. The magnifying lens system includes first and second ends, with the first end coupled to the digital camera and the second end coupled to the eye cup. The magnifying lens system may include one or more lenses.

According to one configuration, the digital camera includes an image sensor. The image sensor may include one or more charge-coupled devices.

According to one feature, the magnifying lens system has a short focal length, and is configured for microscopic imaging of a target structure. The focal length may be between about 0.5 cm and about 15 cm, or between about 1 cm and about 5 cm. The focal length may be about 1 cm, about 2 cm, about 3 cm, about 4 cm, about 5 cm, about 7 cm, about 10 cm, about 12 cm, about 15 cm, or more than about 15 cm. According to another feature, the magnifying lens system provides between about 20 and about 200 times magnification, and may provide between about 30 about 100 times magnification, or between about 40 and about 80 times magnification. The magnifying lens system may provide about 25 times magnification, about 50 times magnification, about 75 times magnification, about 100 times magnification, about 125 times magnification, about 150 times magnification, or about 200 times magnification.

In one configuration, the eye cup is configured for placing over an eye of a user, and may interfit with the face around the eye. The eye cup may prevent environmental light from entering around the eye of the user. The eye cup may be plastic or rubber.

According to various configurations, the device includes a light directed at the target structure. The light may be coupled to the magnifying lens system or the eye cup. The light may be a visible light or a non-visible light, such as in infrared light, or an ultraviolet light. The wavelength of the light may be selected for illuminating a sensor implanted in the target structure. In one configuration, the light is annular and is positioned around at least one of an interior perimeter of the magnifying lens system, an exterior perimeter of the magnifying lens system, or an interior perimeter of the eye cup.

In another configuration, the device also includes a barometer coupled to the magnifying lens system, or coupled to the camera. The device may also include a power supply.

In further configurations, the device includes a filter coupled to the second end of the magnifying lens system. The filter may be a polarizing filter, including a linear polarizing filter or a circular polarizing filter. The filter may be configured to filter out infrared (IR), ultraviolet (UV), or visible light.

According to one configuration, the device includes a transmitter for transmitting an image to an analysis center. In some embodiments, the transmitter may be a USB connection, a cable to the Internet, a wireless internet connection, or a memory, such as a Flashcard memory.

In another aspect, the invention provides a method of performing an eye self-exam. The method includes providing an optical pathway having first and second ends, positioning the first end of the optical pathway over an eye of a user, positioning a digital camera at the second end of the optical pathway, focusing the digital camera on a sensor implanted in the eye, wherein the sensor includes a level indicator, and capturing an image of the level indicator of the sensor.

According to one implementation, the sensor is a pressure sensor and is configured to sense intraocular pressure. The level indicator may display the intraocular pressure level.

In one implementation, the level indicator includes one or more lights. The one or more lights may be used to indicate the level, for example the pressure level. In one example, the color of the light indicates the level of the sensor. In another example, the light indicates whether the level is acceptable or too high by turning on or off, or by flashing or blinking.

In another implementation, the level indicator includes at least one of a dial and a gauge. The dial or gauge may include a backing listing total pressure levels, and may include colored regions to indicate whether pressure is acceptable, borderline, or high.

In still a further implementation, the level indicator includes a digital read-out. The digital read-out may be formed of a light-emitting diode, or it may be a tunable diode laser.

According to various implementations, the optical pathway may include a magnifying lens system. The magnifying lens system may provide between about 2 times magnification and about 200 times magnification of the level indicator, and in one embodiment, provides between about 40 and about 60 times magnification of the level indicator. In various embodiments, the magnifying lens system provides about 25 times magnification, about 50 times magnification, about 75 times magnification, about 100 times magnification, about 125 times magnification, about 150 times magnification, or about 200 times magnification of the level indicator.

In one implementation, the method includes sending the image to an analysis center. Sending the image may include digital transmission of the image. The digital transmission may be wireless.

BRIEF DESCRIPTION OF THE FIGURES

The foregoing and other objects and advantages of the invention will be appreciated more fully from the following further description thereof, with reference to the accompanying drawings. These depicted embodiments are to be understood as illustrative of the invention and not as limiting in any way.

FIGS. 5A-5C depict various optomechanical intraocular sensor reader system housings.

FIGS. 7B-7C depict a digital camera and an adaptor for interfitting with the lens portion of the digital camera.

DETAILED DESCRIPTION

To provide an overall understanding of the invention, certain illustrative embodiments will now be described, including systems, methods and devices for providing intraocular sensor readers for a user to view or image an implant in the user's eye. However, it will be understood by one of ordinary skill in the art that the systems and methods described herein can be adapted and modified for other suitable applications and that such other additions and modifications will not depart from the scope hereof.

Figure 1:
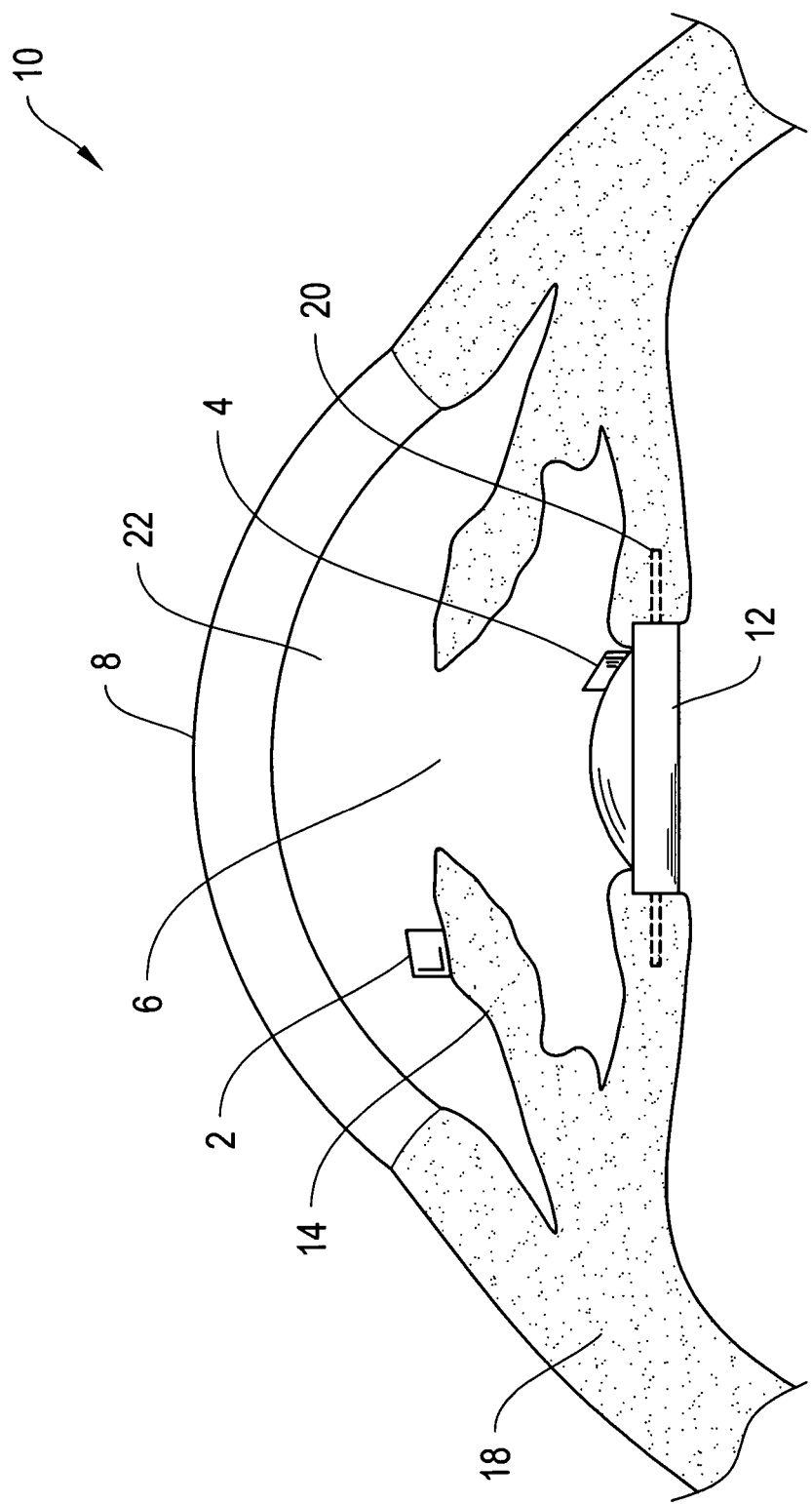
FIG. 1 depicts exemplary intraocular sensors inside an eye.

FIG. 1 depicts a top view of a cross section of an eye 10, including two exemplary intraocular sensors 2 and 4 implanted inside the eye 10. Structurally, the eye 10 includes a cornea 8, a pupil 6, a lens 12, iris 14, sclera 18, a ciliary body 20, and an anterior chamber 22. The cornea 8 is a thin transparent tissue that focuses and transmits light into the eye 10 and through a pupil 6 and the lens 12. The anterior chamber 22 of the eye 10 is bound anteriorly by the cornea 8 and posteriorly by the iris 14 and a lens 12, and is filled with an aqueous solution. In a normal eye, the aqueous solution is continuously removed from the anterior chamber 22. Intraocular pressure is maintained by an intricate balance between secretion and outflow of the aqueous solution. Glaucoma is, in most cases, characterized by an excessive buildup of the aqueous solution in the anterior chamber 22, which leads to an increase in intraocular pressure. Fluids are relatively incompressible, and thus intraocular pressure is distributed relatively uniformly throughout the eye. Thus, sensors placed in the anterior chamber of the eye may accurately measure intraocular pressure.

In addition, sensors may be placed in the eye for a variety of other purposes including, for example, intraocular drug delivery. Sensors may also be implanted for measuring pH, salinity, vascular endothelial growth factor (VEGF), or other properties or substances of the eye. The intraocular sensors 2 and 4 are placed on the iris 14, and the intraocular lens 12, respectively. According to a preferred embodiment, the sensors 2 and 4 are placed out of line-of-sight, such that they do not disrupt the vision of the user, but are placed in a location within the eye such that they may be observable from outside the eye with an appropriate magnification system. In other embodiments, the sensors 2 and 4 may be implanted in any selected location in the eye, including in the cornea 8 and on the interior surface of the cornea 8. The sensors 2 and 4 may be implanted in the eye 10 using any conventional attachment methods, including for example an anchor, suture, hook or other fixation means. According to one embodiment, only one sensor 2 or 4 is implanted in the eye 10. According to one feature, the intraocular sensors 2 and 4 include level indicators, such as the level indicator displays shown in FIG. 2A-2F, which may be observable by looking into the user's eye and viewing the sensors 2 and 4 with a magnification system.

Figure 2A:
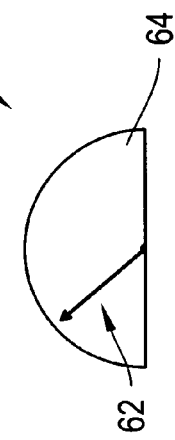
FIGS. 2A-2F depict various exemplary intraocular sensor level indicator displays for the intraocular sensors of FIG. 1.

FIGS. 2A-2F depict various exemplary intraocular sensor level indicator displays 40, 50, 60, 70, 80, and 90. While the intraocular sensor level indicator displays 40, 50, 60, 70, 80, and 90 may indicate the level of any selected attribute, in the following examples, the level indicator displays 40, 50, 60, 70, 80, and 90 are described as intraocular pressure sensor displays. FIG. 2A depicts a level indicator 40 including one light 42. The light 42 indicates whether the intraocular pressure is acceptable or if the pressure is too high. For example, the light may be green if the pressure is acceptable and red if the pressure is too high. Alternatively, the light may be constant if the pressure is acceptable and flashing or blinking if the pressure is too high. In another example, the light may be off if the pressure is acceptable and may turn on when the pressure grows too high. In other embodiments, the light may also be used to indicate a borderline pressure level.

Figure 2B:
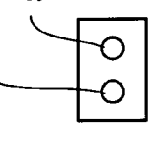

FIG. 2B depicts a level indicator 50 including two lights 52 and 54. The lights 52 and 54 indicate whether the intraocular pressure is acceptable or if the pressure is too high. For example, the lights 52 and 54 may be two different colors, such as green and red. A green light may indicate an acceptable intraocular pressure level, while a red light may indicate a high intraocular pressure level. In other embodiments, any number of lights 52 and 54 may be used to indicate various pressure levels. In one example, yellow light may be included to indicate a borderline pressure level.

Figure 2C:
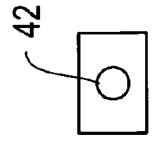

FIG. 2C depicts a level indicator 60 constructed as a gauge or dial, and including a pointer 62 and a semicircular backing 64 which together indicate the intraocular pressure level. The pointer 62 indicates approximate total intraocular pressure based on its position relative to the backing. The backing 64 may include total pressure values. Alternatively, the backing 64 may include colored regions or wedges indicating acceptable pressure, borderline pressure, and high pressure regions.

Figure 2D:
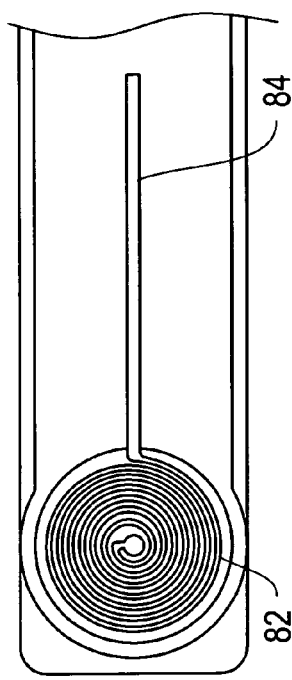

FIG. 2D depicts a level indicator 70 including a digital light-emitting diode (LED) display indicating total intraocular pressure 72 in mmHg. A user or health care professional may interpret the intraocular pressure value 72 to determine whether it is acceptable, borderline, or too high. In one embodiment, the display changes colors depending on the pressure value. For example, if the pressure value is over 21 mmHg, the pressure 72 may be displayed in red, while if the pressure is at or under 21 mmHg, the pressure 72 may be displayed in green. Alternatively, an extra light may be included on the display, which turns on or begins to flash if the pressure is above a predetermined threshold.

Figure 2E:
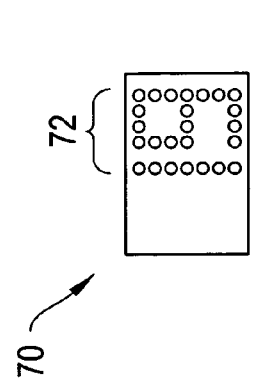

FIG. 2E depicts a level indicator 80 including a spiral 82 and a radially extending arm 84. The spiral 82 may contract or expand depending on the intraocular pressure. Contraction or expansion of the spiral 82 causes the arm 84 to move, and may cause the arm 84 to rotate and thus point toward a different direction. For example, in the illustrative embodiment, expansion of the spiral 82 causes the arm 84 to move upwards while contraction of the spiral 82 causes the arm 84 to move downwards. The movements of the arm 84 and/or the direction towards which the arm 84 points may indicate the IOP pressure.

Figure 2F:
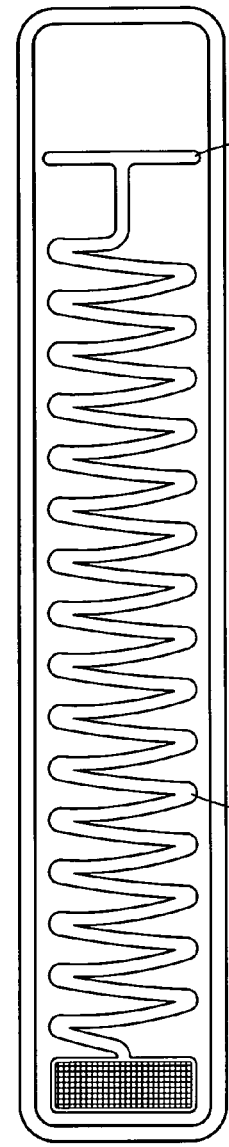

FIG. 2F depicts a level indicator 90 including a spring 92 and a total level t-indicator 94. The spring 92 may contract or expand depending on the intraocular pressure. Contraction or expansion of the spring 92 causes the t-indicator to move, and thus indicate IOP. For example, in the illustrative embodiment, an increase in pressure may cause the spring 92 to expand, thus moving the t-indicator 94 to the right.

According to various embodiments, the level indicator displays 40, 50, 60, 70, 80 and 90 may display any selected type of information depending on the type of sensor implanted. For example, the displays 40, 50, 60, 70, 80 and 90 may indicate the fill level of an intraocular drug delivery system, the status of a drug relieve valve and tube or shunt (i.e., to indicate whether the valve and tube or shunt are clogged), or the level of a monitored intraocular property or substance, such as pH value, salinity, or VEGF.

Once an intraocular sensor including a level indicator display, such as the displays 40, 50, 60, 70, 80 and 90 of FIGS. 2A-2F, has been implanted in an eye, a user may use a reader system to view the sensor and evaluate the output of the sensor. Two exemplary reader systems, an optomechanical sensor reader system 100 and a digital sensor reader system 500, are described below with reference to FIGS. 3A and 7A, respectively.

Figure 3A:
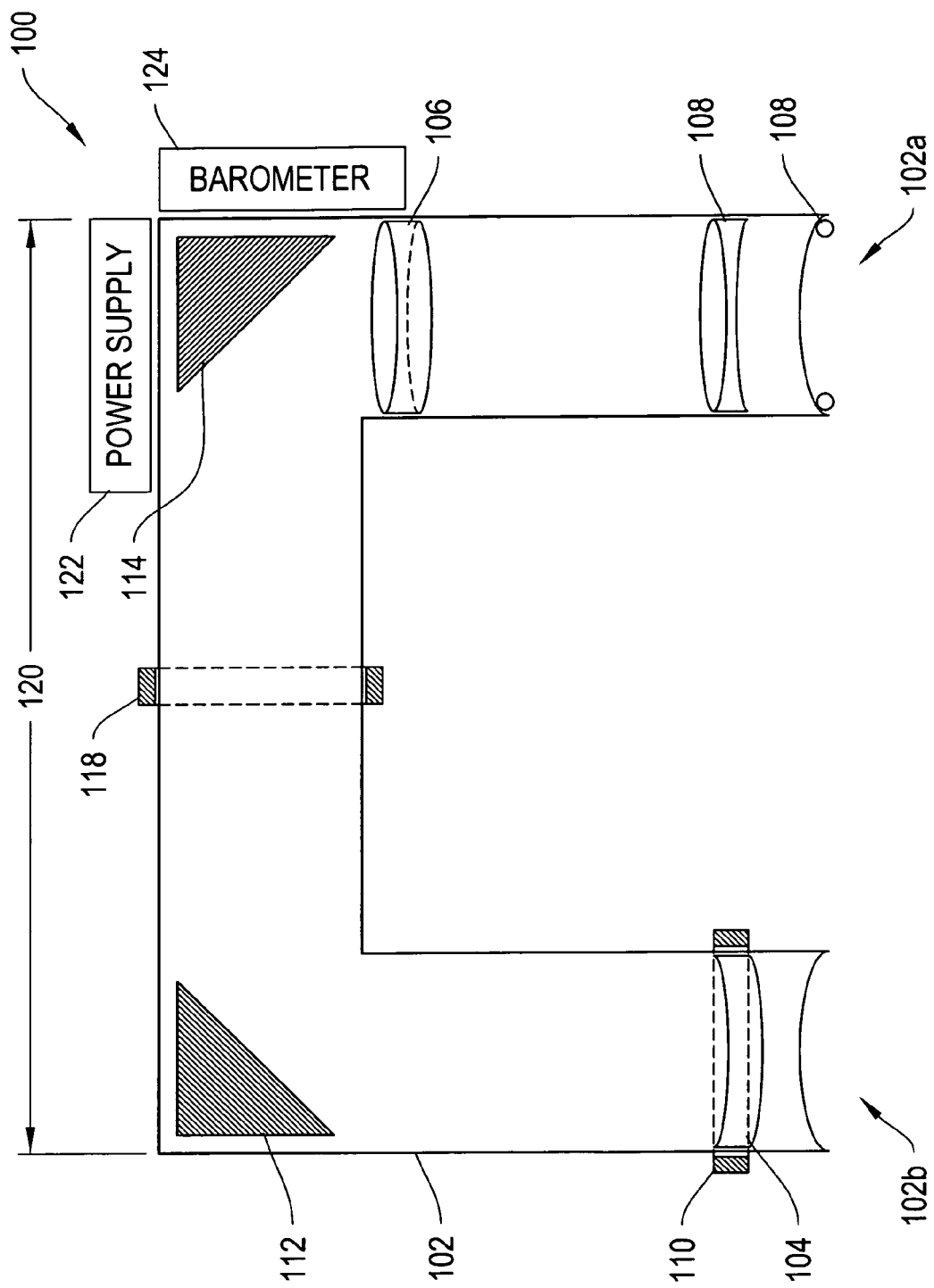
FIGS. 3A and 3B depict a top-view and a front view of an optomechanical intraocular sensor reader system.

FIG. 3A depicts a top view of an optomechanical intraocular sensor reader system 100. The reader system 100 includes a housing 102 and lenses 104, 106 and 108. According to the illustrative embodiment, the reader system 100 also includes two reflective surfaces 112 and 114, which help form an optical pathway through the housing 102, reflecting light entering through a first end 102a of the housing 102 to a second end 102b of the housing 102. In use, a user positions the first 102a and second 102b housing ends of the reader system 100 over each eye, and uses the reader system 100 to view one eye with the other eye.

The housing 102 includes a first end 102a and a second end 102b, and, as seen from a top-view, may be any selected shape, as described in greater detail with respect to FIGS. 5A-5C. The housing includes an interior passageway such that an optical pathway may be formed therethrough. The cross-sectional shape of the housing may also be any selected shape, including for example, circular, elliptical, or polygonal.

The lenses 104, 106 and 108 are configured for magnifying and focusing the view of a target structure, such as sensor displays 40, 50, 60, 70, 80 and 90, located past the first end 102a of the housing 102 as seen from the second end 102b of the housing 102. In one embodiment, the lens 104 is adjustable for focusing the view of the target structure. The reader system 100 includes a focus control 110 for adjusting the lens 104. According to various implementations, the focus control 110 may be manually adjusted by a user, or it may automatically adjust the lens 104. The reader system 100 may include an autofocus sensor coupled with the focus control 110 to automatically adjust the lens 104 to focus the light or the reflected image of a target structure.

The lenses 106 and 108 are configured for magnifying the view of a target structure located at or past the first end 102a of the housing 102, as seen from the second end 102b of the housing 102. In one embodiment, the lenses 106 and 108 provide sufficient magnification for viewing the display of an intraocular sensor. According to various embodiments, the lenses 106 and 108 may provide any selected amount of magnification, including for example, about 2 times magnification, about 5 times magnification, about 10 times magnification, about 20 times magnification, about 30 times magnification, about 40 times magnification, about 50 times magnification, about 60 times magnification, about 70 times magnification, about 80 times magnification, about 90 time magnification, about 100 times magnification, about 120 times magnification, or more than about 120 times magnification. In a preferred embodiment, the lenses 106 and 108 provide between about 40 times magnification and about 80 times magnification.

The lenses 104, 106 and 108 may have any suitable curvature of either of their two surfaces for magnification or focusing of a target structure. Exemplary materials for the lenses 104, 106 and 108 include glass, plastic, and polycarbonate. Note that in various embodiments, the reader system 100 may include any number of lenses, including one lens, two lenses, or more than two lenses. The reader system 100 may also include a filter. The filter may be, for example, a linearly polarizing filter, a circularly polarizing filter, a clear filter, a UV filter, a color correction filter, a color enhancement filter, a color subtraction filter, a cross screen filter, a diffusion filter, a visible light filter, or an infrared filter.

The reader system 100 also includes a width adjuster 118 configured for adjusting the width 120 of the housing 102. For example, the width 120 of the housing 102 may be adjusted such that when the first end 102a of the housing 102 is positioned over the first eye of a user, the second end 102b of the housing is simultaneously positioned over the second eye of the user. Additionally, the housing 102 may be adjustable such that the first and second ends of the housing may lie in different planes (e.g., the first end may be higher than the second end).

In one embodiment, the reader system 100 includes a barometer 124. The barometer 124 is mounted external to the housing 102. The barometer 124 may be integrated into the reader system 100, and it may be mechanically coupled to the housing 102. The barometer 124 may be used to measure external ambient pressure, and it may display the ambient pressure reading externally, or it may be configured to display the ambient pressure in the same view as the target structure inside the eye. The ambient pressure may be used in conjunction with an intraocular pressure sensor to determine IOP.

According to other embodiments, the reader system 100 includes a power supply 122. The power supply 122 may be an electrical power supply such as, for example, a battery, a cable power supply, or a solar power supply.

Figure 3B:
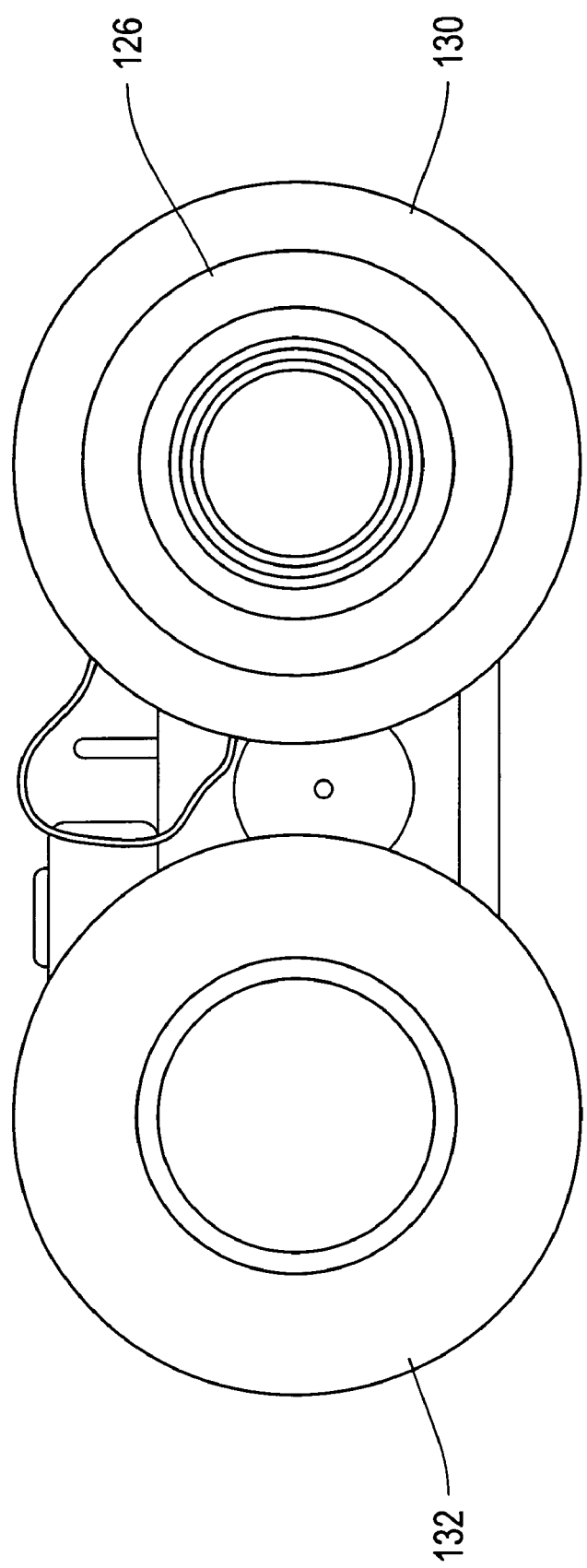

The power supply 122 powers a light 126, as shown in the front view of the reader system 100 in FIG. 3B. The light 126 is directed toward a target structure located at or past the first end 102a of the housing 102. The light 126 is configured to irradiate the target structure without obstructing the optical pathway through the housing 102. The light 126 is positioned about the interior perimeter of the housing 102. In other embodiments, the light 126 may be positioned about the exterior perimeter of the housing 102, or inside the perimeter of an eye piece attached to the first end 102a of the housing 102. As shown in FIG. 3B, the housing 102 has a circular cross-section and the light 126 is annular, and is positioned along the interior perimeter of the housing 102 near the first end 102a of the housing 102. In other examples, the light 126 may include multiple individual lights positioned next to each other or at selected intervals around a perimeter of the housing 102. According to various embodiments, the light may radiate visible or nonvisible light. Exemplary lights include, for example, light-emitting diodes, incandescent light, fluorescent light, ultraviolet light, and infrared light. In one implementation, a nonvisible light is used by the autofocus sensor for automatic focus by the focus control 110. In another implementation, as described in greater detail in U.S. patent application Ser. No. 10/686492, the entire contents of which are hereby incorporated by reference, a nonvisible light may be used to activate a sensor display, such as displays 40, 50, 60, 70, 80 and 90, or to trigger a sensor readout.

As shown in FIG. 3B, the reader system 100 may include an eye piece or eye pieces 130 and 132 configured for interfitting around the eyes of a user. Alternatively, the reader system 100 may include a mask for interfitting around both eyes and over the bridge of the nose of a user. The eye pieces may be made of any suitable material for conforming with the face of the user, including for example, plaster, soft plastic, rubber, or spongy material. According to one feature, when a user places the eye pieces around their eyes, environmental light is blocked out of the housing 102.

The reader system 100 is a handheld device which may be held up against the eyes of the user. In other embodiments, the reader system 100 may be designed to be placed on a stable surface, or into a stand on a stable surface, such that the user may use the reader system 100 by placing the ocular facial area over the eye pieces, without holding the reader system 100.

According to one feature, the reader system 100 may be turned over, such that it may be used to view the right eye with the left eye and to view the left eye with the right eye.

In one embodiment, the reader system 100 includes a beam-splitter such that the system 100 may be used as described above, with the view of the target structure visible from the second end 102b of the housing 102, and additionally, with an identical view of the target structure transmitted to an image sensor coupled to the reader system 100. The image sensor captures an image of the view of the target structure. The image sensor may be integrated into a digital camera system, and may function in a manner substantially similar to the digital reader system 500 of FIG. 7A.

Figure 4:
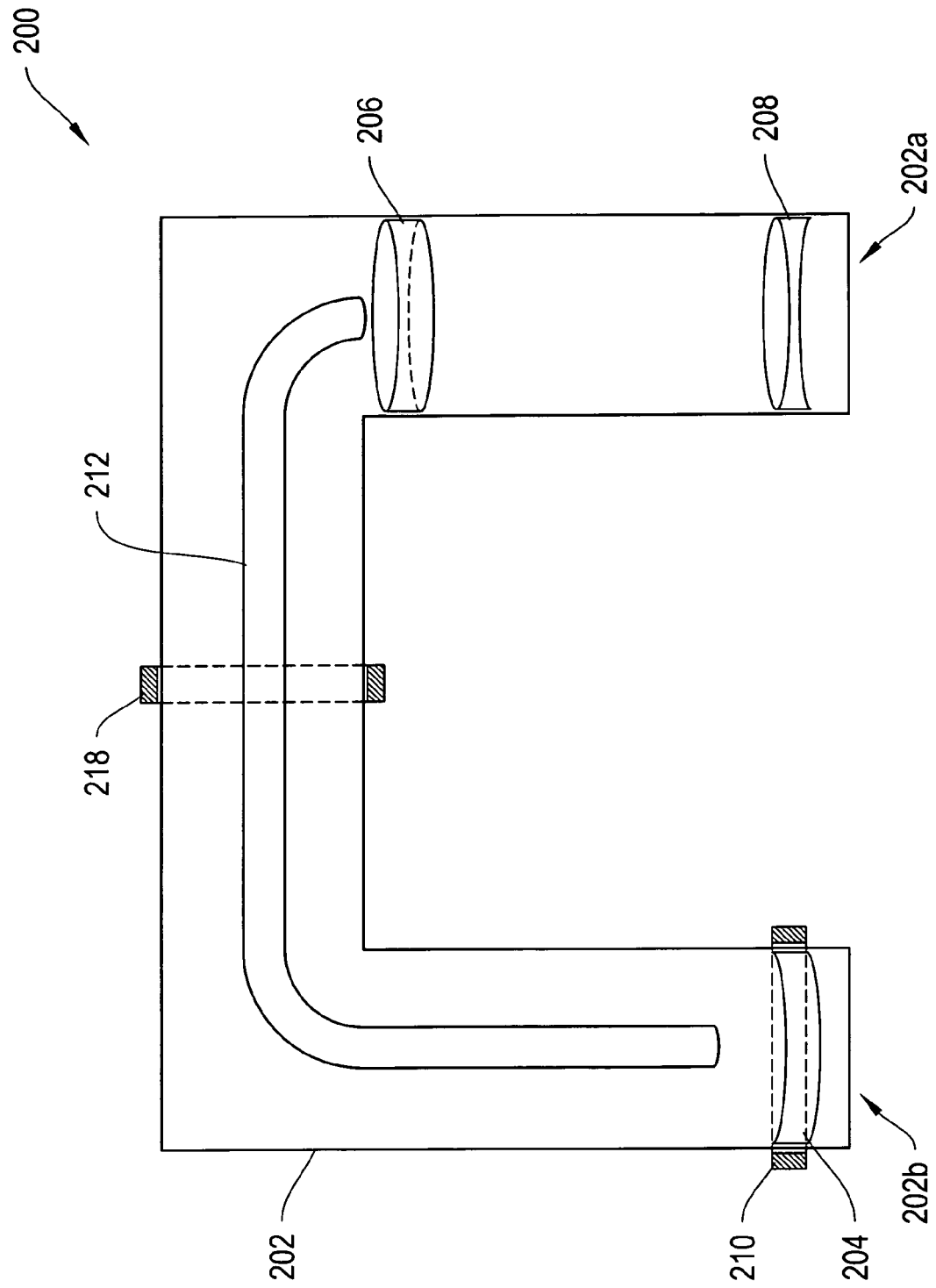
FIG. 4 depicts an alternative optomechanical intraocular sensor reader system.

FIG. 4 depicts an alternative optomechanical intraocular sensor reader system 200. The reader system 200 includes a housing 202 and lenses 204, 206 and 208. The reader system 200 also includes an optical fiber 212, which directs light entering through a first end 202a of the housing 202 to a second end 202b of the housing 202, thus becoming a part of an optical pathway formed through the interior of the housing 202.

The optical fiber 212 is a coherent bundle of fibers, similar to the optical fibers used in medical endoscopes. As shown in the illustrative embodiment, the optical fiber 212 transmits light or an image from a distal side of the lens 206 to a distal side of the lens 204. According to another embodiment, one or more lenses may be inserted at one or more of the ends of the optical fiber 212. The optical fiber may be constructed of any selected optical fiber material, including silica, glass, fluorozirconate glass, fluoroaluminate glass, chalcogenide glass, and plastic.

The housing 202 is substantially the same as the housing 102 of FIG. 3, and the lenses 204, 206 and 208 are substantially the same as lenses 104, 106 and 108 of FIG. 3, respectively. The reader system 200 also includes a focus control 210 and a width adjuster 218, which may be substantially the same as the focus control 110 and the width adjuster 118 of FIG. 3, respectively. The reader system 200 may also include a light for irradiating a target structure at or past a first end 202a of the housing 202, a barometer, and/or a power supply.

FIGS. 5A-5C depict various optomechanical intraocular sensor reader system housings 300, 310, and 320. FIG. 5A depicts a housing 300 having a semi-elliptical shape. The housing 300 may alternatively have a semi-circular shape. FIG. 5B depicts a housing 310 having a v-shape. FIG. 5C depicts a polygonal housing 320. According to various embodiments, the housing 320 may have any selected number of sides, including 3 sides, 4 sides, 5 sides, 6 sides, 7 sides, 8 sides, and more than 8 sides. The sides of the housing 320 may be any selected length, and may be joined at any selected angles so long as the first 320a and second 320b ends of the housing 320 are configured for placing over the eyes of a user. According to one feature, the housings 300, 310, and 320 are configured such that an optical pathway may be formed from a first end 300a, 310a, and 320a to a second end 300b, 310b, and 320b of the housings 300, 310, and 320, respectively. According to one feature, an optical pathway permits a user to view a target structure at a first end 300a, 310a, or 320a of a housing 300, 310, or 320, from the second end 300b, 310b, or 320b of the housing 300, 310, or 320, respectively. In one embodiment, the housings 300, 310, or 320 may be adjustable such that the first and second ends may lie in different planes.

Figure 6:
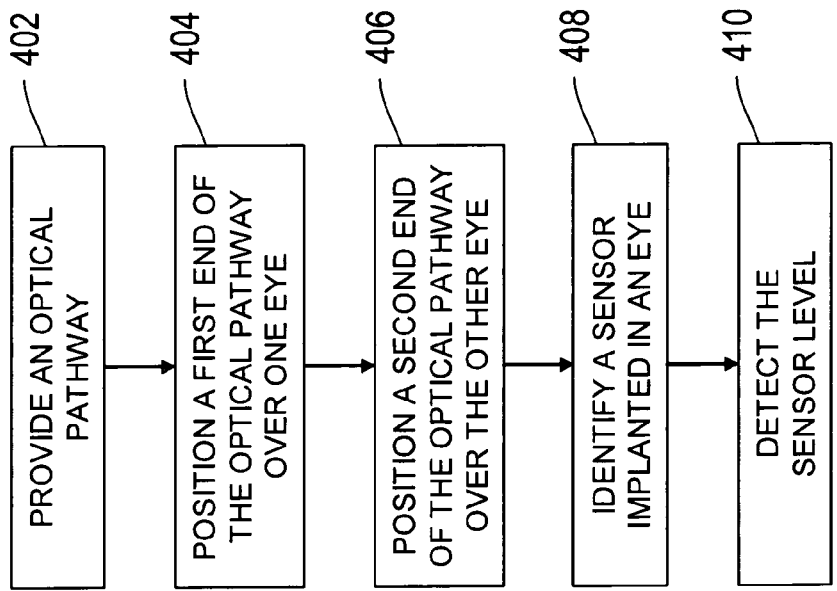
FIG. 6 is a flow chart of a method for performing a self-evaluation of an intraocular sensor.

FIG. 6 is a flow chart of a method 400 for performing a self-evaluation of an intraocular sensor. The method 400 begins with providing an optical pathway (step 402) having first and second ends. According to one embodiment, the optical pathway may be provided by one of the reader systems 100 or 200 of FIGS. 3A and 4. The first end of the optical pathway is positioned over a first eye of a user (step 404), while the second end of the optical pathway is positioned over the second eye of the user (step 406). The user may then utilize the optical pathway to view a target structure in the first eye with the second eye. According to the method 400, the user identifies a sensor implanted in the first eye (step 408). According to one feature, the sensor includes a level indicator, which may indicate the intraocular pressure level. The level indicator may have an indicator display, such as the displays 40, 50, 60, 70, 80 and 90 of FIGS. 2A-2F. Once the user has identified the sensor, the user may then detect the sensor level (step 410).

In an alternative embodiment, the systems 100 and 200 of FIGS. 3A and 4 may be used by one user to evaluate the ocular sensor of another user. In this embodiment, the first end of the optical pathway is positioned over the eye to be evaluated, and the second end is positioned over the eye of the viewer, such that the viewer can see the target structure in the eye of the other user.

Figure 7A:
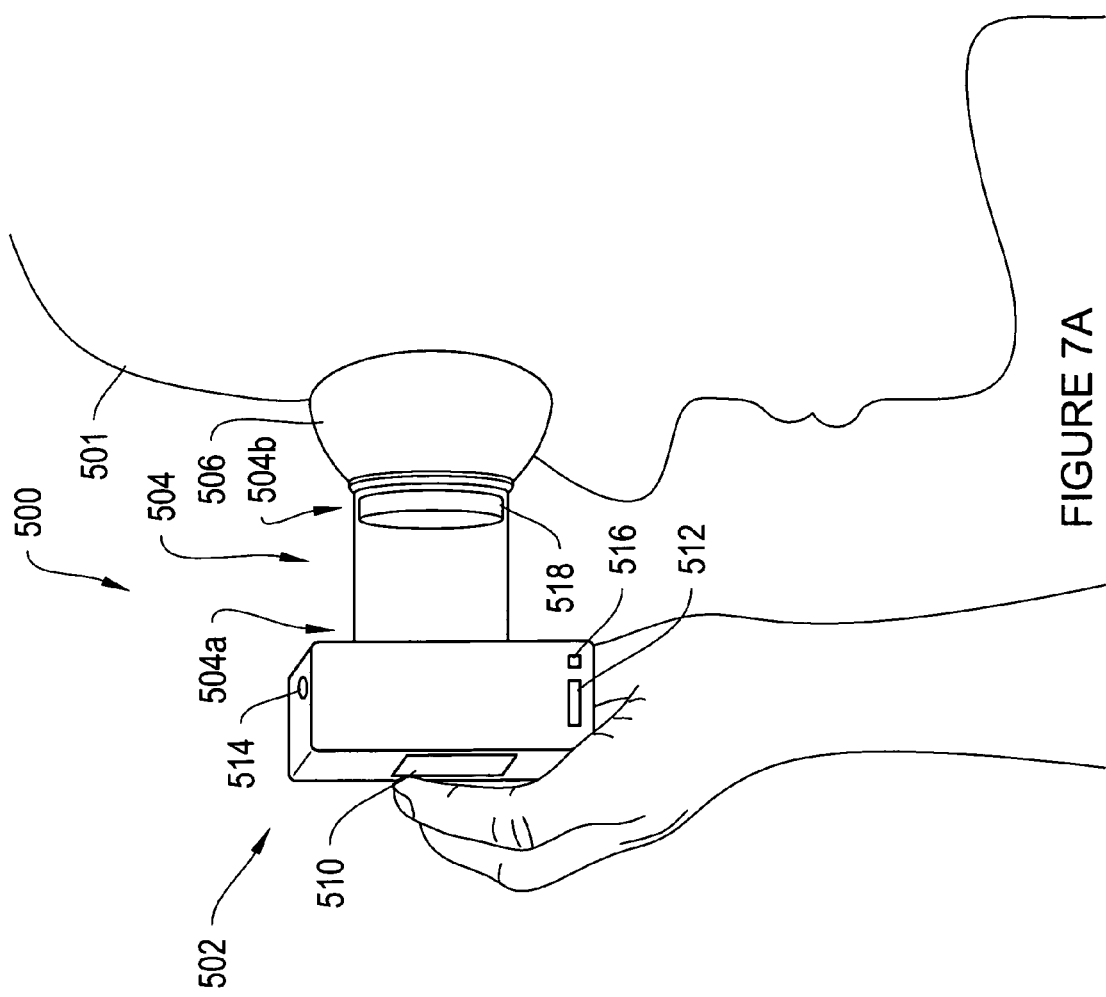
FIG. 7A depicts a digital intraocular sensor reader system.

FIG. 7A depicts a digital intraocular sensor reader system 500 positioned over the eye of a user 501. The reader system 500 includes a digital camera 502, a magnifying lens system 504, and an eye cup 506. The digital camera 502 uses the magnifying lens 504 to focus on and capture an image of a target structure.

Digital cameras generally have optical and digital zooming capabilities, including for example, tele-zoom lens systems and digital interpolation. Additionally, many digital cameras include a macro-mode for shooting images up-close, usually from a distance of about 20 cm from the target object. Also, many digital cameras capture images with a resolution of about 5 or more megapixels.

The digital camera 502 may be a conventional consumer digital camera. The digital camera 502 includes a viewing screen 510, for example, an LCD, for viewing previously captured images. The digital camera 502 also includes a memory card 512 for storing images. According to one feature of the digital camera 502, a user may select to view an image in its entirety on the viewing screen, or the user may zoom into the image to view a particular portion of the image in greater detail. According to one example, the image on the viewing screen 5 10 may be zoomed in at least as far as the native (uninterpolated) resolution of the camera allows. The digital camera 502 also includes a button 514, which, when depressed, causes the camera 502 to take a picture. According to one feature, the digital camera 502 includes an image sensor configured to convert the input image to an electrical signal. The image sensor may be any selected image sensor, and may include for example, one or more charge coupled devices (CCD's), complementary metal-oxide semiconductor (CMOS) sensors, active pixel sensors, Bayer sensors, Foveon X3 sensors, or 3CCD sensors. According to various embodiments, the image sensor may have any selected resolution suitable for imaging a target structure, including for example, about 1 megapixel, about 2 megapixels, about 3 megapixels, about 4 megapixels, about 5 megapixels, about 6 megapixels, about 7 megapixels, about 8 megapixels, about 9 megapixels, about 10 megapixels, or more than about 10 megapixels.

The memory card 512 may be an electronic flash memory data storage device, including for example, SD/MMC, Memory Stick, xD-Picture Card, SmartMedia and CompactFlash. The memory card 512 stores captured images, which may be transferred to an external computer system or database. Captured images may be transferred by removing the memory card from the digital camera 502 and coupling it to an external computer system. Alternatively, the camera 502 may include a port 516, and may be connected to an external computer system via a cable (e.g., a USB or FIREWIRE™ IEEE 1394 standard cable) to transfer captured images, or the captured images may be wirelessly transmitted to an external computer system or internet address. The camera may be an Internet Protocol (IP) camera, and thus include an IP address. An IP camera may connect directly with the internet. The captured images may be time and/or date-stamped by the digital camera 502.

According to one embodiment, captured images may be transmitted to an analysis center. In one example, a health care professional may analyze the image of an ocular pressure sensor sent either directly from a reader system 500 transmitter, or from an image downloaded from the memory card 512, or transmitted over the internet (e.g., via email). The health care professional may determine the intraocular pressure level from the image. According to one advantage, this system may allow a user to have frequent intraocular pressure level check-ups without requiring frequent visits to a health care professional.

The magnifying lens system 504 includes first 504a and second 504b ends, and at least one lens 518. According to the illustrative embodiment, the first end 504a is coupled to the digital camera 502, while the second end 504b is coupled to the eye cup 506.

According to one embodiment, as shown in FIGS. 7B and 7C, an adapter 520 is interfitted around and/or attached to the protruding lens portion 522 of a digital camera, and the first end 504a of the magnifying lens system 504 is coupled to the adapter 520. FIG. 7B depicts the adaptor 520 separate from the digital camera 502, while FIG. 7C depicts the adaptor 520 interfitted around the lens portion of the digital camera 502. Using the adapter 520, a conventional two-part macro lens may be attached to, for example screwed onto, the digital camera lens. The adaptor 520 may be threaded or magnetic for coupling with the macro lens. According to one feature, the adaptor 520 is configured for providing a standard SLR camera lens attachment mechanism to a compact digital camera. The macro lens acts as a magnifying lens system 504, enabling a conventional digital camera to capture an in-focus image of an object that is between about 1 cm and about 10 cm away from the second end 504b of the magnifying lens system 504.

According to various embodiments, a variety of lens systems may be attached to the adapter 520, and any selected lens system may be used in conjunction with the digital camera 502 in the digital reader system 500. Additionally, the adapter 520 may be modified and tailored to fit a variety of digital cameras and camcorders. The adapter 520 may be mounted on the protruding lens of a camera, or on the body of the camera around the lens. According to one feature, an adaptor 520 positioned on the body of the camera includes space for the camera lens to protrude and perform focusing and zooming operations. In various embodiments, the adapter 520 may be mounted to the camera magnetically, with an adhesive, screwed on, or snap-fitted. The adaptor 520 interfits snugly with the camera 502.

The magnifying lens system 504 has a short focal length for microscopic imaging of a target structure. The focal length may be between about 0.5 cm and about 15 cm, and it may be about 1 cm, about 2 cm, about 3 cm, about 4 cm, about 5 cm, about 6 cm, about 7 cm, about 8 cm, about 9 cm, about 10 cm, about 12 cm, about 15 cm, or more than about 15 cm.

The magnifying lens system 504 may provide any selected amount of magnification, including between about 2 times magnification and about 200 times magnification, and may provide between about 40 times magnification and about 60 times magnification. The magnifying lens system 504 may provide about 5 times magnification, about 10 times magnification, about 20 times magnification, about 30 times magnification, about 40 times magnification, about 50 times magnification, about 60 times magnification, about 70 times magnification, about 80 times magnification, about 90 times magnification, about 100 times magnification, or more than about 100 times magnification.

According to one embodiment, the magnifying lens system 504 includes a filter. The filter may be, for example, a linearly polarizing filter, a circularly polarizing filter, a clear filter, a UV filter, a color correction filter, a color enhancement filter, a color subtraction filter, a cross screen filter, a diffusion filter, a visible light filter, or an infrared filter. The filter may be positioned at the second end 504b of the magnifying lens system 504, or it may be positioned in any selected location in the magnifying lens system 504. The filter may be constructed from glass, resin plastics similar to those used for eyeglasses (such as CR39), polyester, or gelatin, and it may include a material such as a film or nylon netting sandwiched between two pieces of clear glass or plastic. According to some implementations in which an eye is imaged, the shiny cornea of the eye may produce glare, which may be filtered out using a polarized filter.

The magnifying lens system 504 may also include a diffraction element or prism. This element separates out incoming light into its constituent wavelengths, allowing for hyperspectral analysis of the eye. In one example, the hyperspectral information can be analyzed, for example, to determine oxygen levels in various areas of the eye.

In other embodiments, the reader system 500 may include a housing with an optical fiber in place of the magnifying lens system. The optical fiber may be substantially the same as the optical fiber 212 of FIG. 4. In this embodiment, the housing may be flexible, such that one end of the housing may be positioned in a different plane from the other end of the housing.

The reader system 500 includes an eye cup 506 for placing over an eye. The eye cup may be coupled to the second end of the magnifying lens system 504 by, for example, screwing, snapping, magnetic attachment, or an adhesive. According to one embodiment, the eye cup 506 is configured to prevent environmental light from entering around its edges, and thus to prevent environmental light from entering the magnifying lens system 504, when the eye cup 506 is placed on a user's face. The eye cup may be constructed of any suitable material for conforming with a user's face and thus blocking environmental light from entering the lens system 504, including for example plastic, soft plastic, rubber, or a spongy material.

Figure 7D:
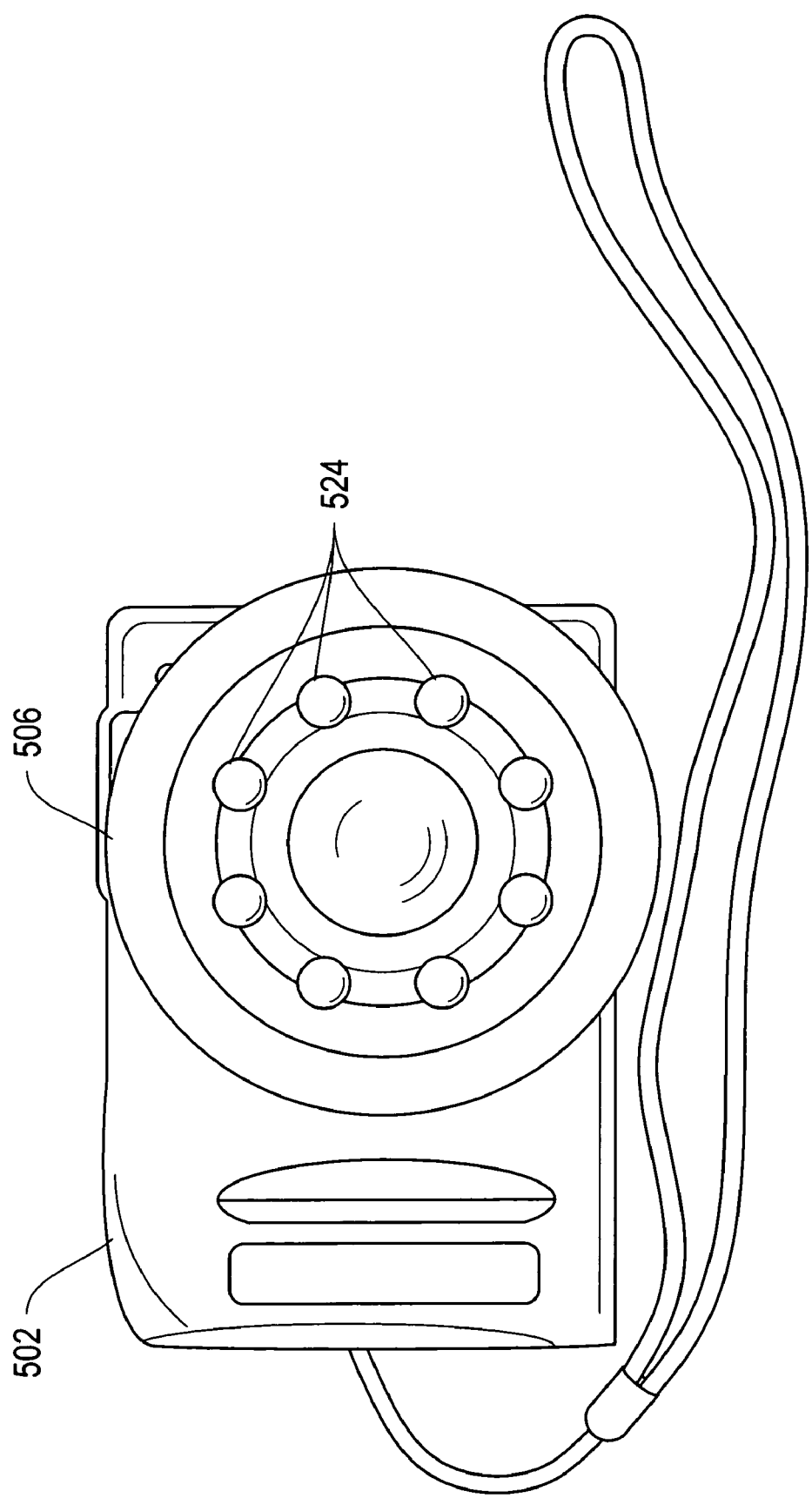
FIG. 7D depicts a front view of a digital intraocular sensor reader system.

According to some embodiments, as shown in FIG. 7D, the reader system 500 includes a light 524. The light 524 of FIG. 7D includes multiple individual lights places around the interior perimeter of the magnifying lens system 504. The light 524 is directed towards a target structure, for example the eye of a user, or the intraocular area of the user. According to one feature, the light does not obstruct the optical pathway of the digital camera 502 through the magnifying lens system 504 to the target structure. In other embodiments, the light may be positioned around the exterior perimeter of the magnifying lens system 504, and/or it may be positioned around the interior perimeter of the eye cup 506. The light may be annular, or it may include multiple lights positioned around the perimeter of the magnifying lens system and/or eye cup. In one embodiment, the light is distinguishable to the image sensor of the digital camera 502, but is not visible to the user. For example, the light may be an infrared light or an ultraviolet light. According to other examples, the light may be any selected type of light, including for example, light-emitting diodes, incandescent light, and fluorescent light.

According to another embodiment, the digital sensor reader system 500 is placed in a stand or designed for stable positioning on a table, such that the system 500 becomes a desktop or tabletop device, and the user does not need to hold the device to an eye. In this embodiment, the user may simply place the ocular facial area over the eye cup 506. In an alternative embodiment, the reader system 500 may include a larger eye mask that covers both eyes and encompasses the bridge of the nose. In this embodiment, the reader system 500 may be designed to capture an image of both eyes simultaneously, or a user may select which eye is to be imaged. According to one feature, the system may be networked with or coupled to a display for displaying the captured image. Thus, a user may view the captured image on the display to ensure that the eye or eyes were open when the picture was taken. The reader system may then transmit the image either directly or via a computer system to an internet or email address for analysis. According to one feature, the transmitted image is time and/or date-stamped.

According to one embodiment, the digital reader system 500 takes a snapshot of an eye including an ocular sensor, and image processing algorithms locate the sensor in the internal image. The image processing algorithms extract the current sensor setting, and produce a digital output of the sensor level. For an IOP sensor, the image processing algorithms may produce a digital output of the IOP level and the external barometric pressure, measured at the time of the snapshot. According to one feature, this embodiment does not include a display 510.

According to various implementations, in addition to monitoring implanted ocular sensors, the reader system 500 may be used to observe iris tissue and iris tissue pathologies, to observe the anterior chamber of the eye, or to observe the fundus of the eye and detect fundus anomalies. The reader system 500 may also be used to observe fluorescence in the eye tissue, either directly or after injection of a specific dye, and the fluorescence may be visible with or without excitation (e.g., with UV light).

Figure 8:
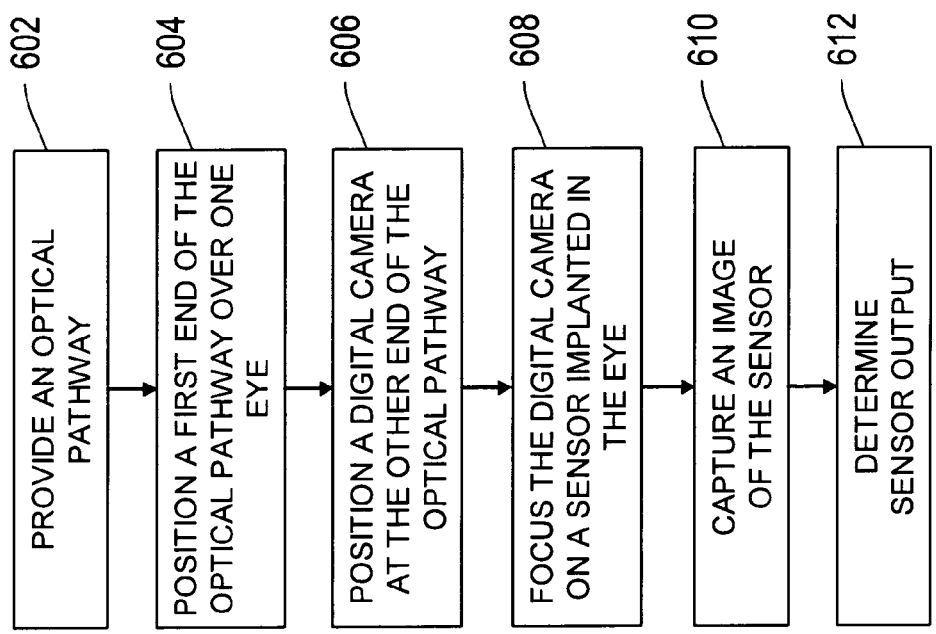
FIG. 8 is a flow chart of a method for capturing an image of a user's eye, including an image of an intraocular sensor implanted in the eye.

FIG. 8 is a flow chart of a method 600 for capturing an image of a user's eye, including an image of an intraocular sensor implanted in the eye. The method begins by providing an optical pathway (step 602) having first and second ends. According to one example, the optical pathway is provided by a digital sensor reader system, such as the system 500 of FIG. 7. A first end of the optical pathway is positioned over an eye of a user (step 604). The second end of the optical pathway includes a digital camera (step 606). In one embodiment, the second end of the optical pathway ends with the image sensor of the digital camera. The digital camera is focused on a sensor implanted in the user's eye (step 608). In one embodiment, the sensor includes a level indicator, and the digital camera is focused on the level indicator. The digital camera is used to capture an image of the sensor (step 610). The image may then be used to determine the level of the sensor (612). In one embodiment, the user may analyze the image to determine sensor level. In another embodiment, the image may be transmitted to a health care professional for analysis of sensor level. In still a further embodiment, the image may be transmitted to an analysis center for processing. For example, given the imaged sensor, the analysis center may extract the sensor level reading and forward the reading on to a health care professional.

Those skilled in the art will know or be able to ascertain using no more than routine experimentation, many equivalents to the embodiments and practices described herein. Accordingly, it will be understood that the invention is not to be limited to the embodiments dislosed herein, but is to be

What is claimed is:

1. A method of performing an eye self-exam comprising:
providing an optical pathway having first and second ends;
positioning the first end of the optical pathway over a first eye of a user;
positioning the second end of the optical pathway over a second eye of the user; and
performing the eye self-exam by the user by
  i) identifying, with the second eye, through the optical pathway, a sensor implanted in the first eye, wherein the sensor includes a level indicator; and
  ii) detecting a level of the sensor.

2. The method of claim 1, wherein the sensor is a pressure sensor.

3. The method of claim 1, wherein the level is a pressure level.

4. The method of claim 1, wherein the level indicator comprises at least one light.

5. The method of claim 4, wherein the color of the light indicates the level of the sensor.

6. The method of claim 1, wherein the level indicator comprises one of a dial and a gauge.

7. The method of claim 1, wherein the level indicator comprises a digital read-out.

8. The method of claim 7, wherein the digital read-out comprises a light-emitting diode.

9. The method of claim 1, wherein the optical pathway comprises at least one reflective surface.

10. The method of claim 1, wherein the optical pathway comprises an optical fiber.

11. A method of performing an eye exam comprising:
providing an optical pathway having first and second ends;
positioning the first end of the optical pathway over an eye of a user;
positioning a digital camera at the second end of the optical pathway; and conducting the eye exam by
  i) focusing the digital camera through the optical pathway on a sensor implanted in the eye, wherein the sensor includes a level indicator; and
  ii) capturing an image of the level indicator of the sensor by the digital camera.

12. The method of claim 11, wherein the sensor is a pressure sensor.

13. The method of claim 11, wherein the level indicator displays a pressure level.

14. The method of claim 11, wherein the level indicator comprises at least one light.

15. The method of claim 14, wherein the color of the light indicates the level of the sensor.

16. The method of claim 11, wherein the level indicator comprises one of a dial and a gauge.

17. The method of claim 11, wherein the level indicator comprises a digital read-out.

18. The method of claim 17, wherein the digital read-out comprises a light-emitting diode.

19. The method of claim 11, wherein the optical pathway comprises a magnifying lens system.

20. The method of claim 19, wherein the magnifying lens system provides about 50 times magnification of the level indicator.

21. The method of claim 19, wherein the magnifying lens system provides between 40 times magnification and 80 times magnification.

22. The method of claim 11, further comprising sending the image to an analysis center.

23. The method of claim 22, wherein sending comprises digital transmission of the image.

24. The method of claim 23, wherein the digital transmission is wireless.

25. The method of claim 11, wherein the method is performed by the user.

* * * * *